(12) United States Patent
Vetter et al.

(10) Patent No.: US 9,999,758 B2
(45) Date of Patent: Jun. 19, 2018

(54) IN-SITU MATERIAL DELIVERY DEVICES AND METHODS

(71) Applicant: TRANSMED7, LLC, Portola Valley, CA (US)

(72) Inventors: James William Vetter, Portola Valley, CA (US); Eugene H Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 225 days.

(21) Appl. No.: 14/852,901

(22) Filed: Sep. 14, 2015

(65) Prior Publication Data

US 2016/0166817 A1    Jun. 16, 2016

Related U.S. Application Data

(60) Provisional application No. 62/052,591, filed on Sep. 19, 2014.

(51) Int. Cl.
*A61M 37/00* (2006.01)
*A61M 5/00* (2006.01)
(Continued)

(52) U.S. Cl.
CPC ......... *A61M 37/00* (2013.01); *A61B 17/3468* (2013.01); *A61B 17/3478* (2013.01);
(Continued)

(58) Field of Classification Search
CPC .............. A61M 37/00; A61M 37/0069; A61M 31/007; A61B 17/3468; A61B 10/06
(Continued)

(56) References Cited

U.S. PATENT DOCUMENTS

| 5,174,300 A | 12/1992 | Bales et al. |
| 5,251,641 A | 10/1993 | Xavier |

(Continued)

OTHER PUBLICATIONS

International Search Report and Written Opinion in PCT/US15/50868, dated Dec. 18, 2015.
(Continued)

*Primary Examiner* — Andrew Gilbert
*Assistant Examiner* — Courtney Fredrickson
(74) *Attorney, Agent, or Firm* — Young Law Firm, P.C.

(57) ABSTRACT

An in-situ material delivery device for handheld, stereotactic table or MRI stage use may comprise a work element configured to selectively open and close at least one articulable beak configured to penetrate tissue to a target delivery site, or follow a central lumen of another device or other guiding modality, and then to deliver selected materials. Such a device may deliver a variety of materials such as markers, radio-active pellets, medications, other devices, and other materials of solid, liquid or gaseous form to a target site, and materials of similar nature may also be captured and removed from a target site. A single tube with or without coatings or an inner sheath and an outer sheath which may be co-axially disposed relative to a work element may be configured to actuate a beak or beaks and internal delivery mechanisms simultaneously. One embodiment of this device may be applicable to field use or one time use.

20 Claims, 10 Drawing Sheets

(51) Int. Cl.
*A61B 17/34* (2006.01)
*A61N 5/10* (2006.01)
*A61B 10/06* (2006.01)

(52) U.S. Cl.
CPC .......... *A61M 5/00* (2013.01); *A61M 37/0069* (2013.01); *A61N 5/1007* (2013.01); *A61B 10/06* (2013.01); *A61N 2005/1008* (2013.01)

(58) Field of Classification Search
USPC ............................ 604/57, 59, 60, 61, 62, 63
See application file for complete search history.

(56) References Cited

U.S. PATENT DOCUMENTS

| | | | |
|---|---|---|---|
| 5,304,119 A * | 4/1994 | Balaban | A61M 37/0069 604/107 |
| 5,415,169 A | 5/1995 | Siczek et al. | |
| 5,526,822 A | 6/1996 | Burbank | |
| 5,873,886 A | 2/1999 | Larsen et al. | |
| 6,197,324 B1 | 3/2001 | Crittenden | |
| 2002/0165580 A1 | 11/2002 | Zwiefel et al. | |
| 2003/0032955 A1 | 2/2003 | Mulier | |
| 2003/0208153 A1 | 11/2003 | Stenzel | |
| 2005/0070885 A1 | 5/2005 | Nobis et al. | |
| 2005/0209564 A1 | 9/2005 | Bonner et al. | |
| 2006/0155163 A1 | 7/2006 | Yachia et al. | |
| 2007/0186923 A1 * | 8/2007 | Poutiatine | A61J 7/0038 128/200.14 |
| 2008/0033280 A1 | 2/2008 | Lubock et al. | |
| 2009/0287114 A1 | 11/2009 | Lee | |
| 2010/0022952 A1 | 1/2010 | Solomon et al. | |
| 2010/0121153 A1 | 5/2010 | To | |
| 2011/0245725 A1 | 10/2011 | Flatland et al. | |
| 2013/0041256 A1 | 2/2013 | Flebig | |
| 2013/0096459 A1 | 4/2013 | Vetter | |
| 2014/0213932 A1 | 7/2014 | Knoll et al. | |

OTHER PUBLICATIONS

USPTO Office Action dated Oct. 16, 2015 in U.S. Appl. No. 14/052,727.
USPTO Office Action dated Oct. 9, 2015 in U.S. Appl. No. 14/853,806.
International Search Report and Written Opinion in PCT/US14/039676, dated Apr. 23, 2015.
International Search Report and Written Opinion in PCT/US14/039688, dated Apr. 23, 2015.
USPTO Office Action dated Oct. 30, 2015 in U.S. Appl. No. 13/903,800.
International Search Report and Written Opinion dated Apr. 1, 2016 in PCT/US2015/50118.

* cited by examiner

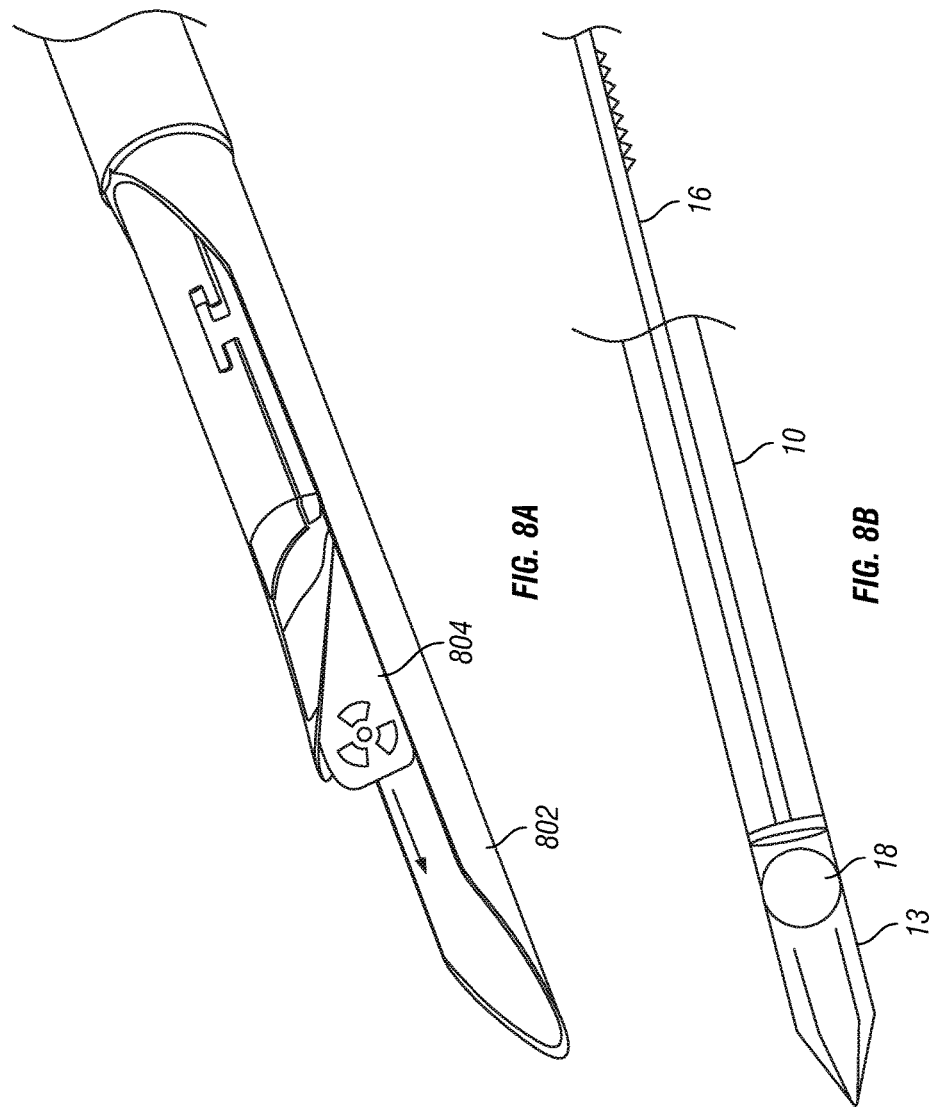

IN-SITU MATERIAL DELIVERY DEVICES AND METHODS

CROSS-REFERENCE TO RELATED APPLICATIONS

This application claims priority under 35 U.S.C. § 119(e) of Provisional Application No. 62/052,591, filed Sep. 19, 2014, which application is hereby incorporated herein by reference in its entirety.

BACKGROUND

Embodiments relate to medical devices and methods. More particularly, embodiments relate to hand-held or mounted single insertion, single or multiple delivery in-situ material delivery devices and corresponding methods for delivering multiple and/or a variety of materials in-situ using a single percutaneous insertion or multiple insertions.

SUMMARY

Embodiments are drawn to various medical devices and methods that are used for in-situ material delivery or removal procedures. According to one embodiment, an in-situ delivery device may be configured to deliver single or multiple materials or discrete items such as markers, nanostructures, medications, implant materials, luminescent dyes, optical scanning devices, light sources or other materials or devices, during a single insertion through the skin (percutaneous procedure). Alternatively the present devices may be configured for or used to deliver other materials such as, for example, a predetermined amount of paste or other non-discrete materials. The delivery or removal may be made into the, for example, soft or hard tissue area of the body, including areas from which a biopsy, excision or other procedure may have been previously effected. Embodiments may comprise structures and functionality for different phases of a multi-phase material delivery procedure, which procedure may be performed by hand or by attachment to a stereotactic table stage or Magnetic Resonance Imaging (MRI) stage. The procedure may be made through the central lumen of a compatible biopsy device or vascular structure, for example. For example, embodiments may be configured for pre-treating abnormal tissue or, for example, for the delivery of tracer materials for tracking the potential spread or flow patterns through which abnormal tissues (such as cancerous tissues) may metastasize. Embodiments may also be configured for an intra-procedure delivery of medications that may anesthetize tissues at the site, or for the delivery of other therapeutic agents such as, for example, pro-coagulants. The device may, according to one embodiment be configured for the delivery of post-procedure materials such as medications, implantable materials for cosmetic purposes and other implantable elements such as marking devices for later imaging reference. Embodiments may be specifically configured to deliver a variety of imaging devices or components, such as fiber optic cables, OCT scanners, ultrasound imagers or cameras of appropriate size. One use of the device according to embodiments is for the delivery of materials to a target tissue site. Another use of the device according to embodiments is for removal of materials, such as fluids, cells, or previously placed markers or radio- or chemically-active pellets or capsules, for example, from a target tissue site, with or without the addition of flush or vacuum subsystems which may be easily attached and function through the central lumen of the device described herein. Embodiments of the material delivery device may be configured to be portable, disposable or reusable and may further be powered, electrically, mechanically-, hydraulically-, pneumatically- and/or manually-powered and operated.

BRIEF DESCRIPTION OF THE DRAWINGS

FIG. 8A shows a scoopula-shaped element used in combination with a work element of a device according to one embodiment.

FIG. 8B shows details of one embodiment of a material delivery device.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

Figure 1:
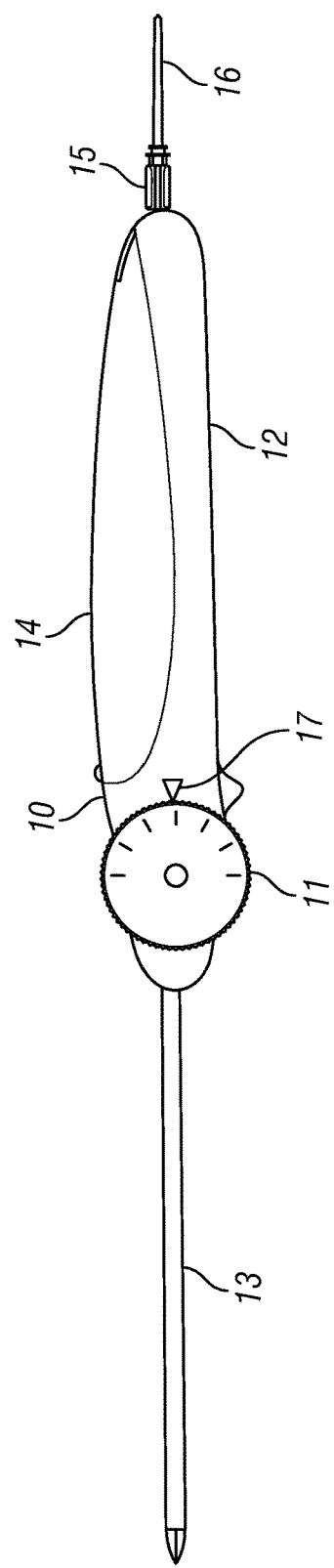
FIG. 1 is a perspective side view of an in-situ material delivery device according to one embodiment.

FIG. 1 shows a side perspective view of a device according to one embodiment. The device may be configured for in vivo delivery of any or all of a variety of medications, liquids, gases, radio-active pellets, capsules, lysing agents, congealing agents, markers, stents, analgesics or clotting agents, among other materials. According to embodiments, the device may comprise a single tube or a single tube with a coaxially-disposed inner or outer tubes or coatings. The device may comprise materials such as stainless steel hypodermic tube ("hypo tube"), having laser cuts therein to define a monolithic work element 13. The work element 13 may comprise one or more beaks, a living hinge that attaches to or is a continuation of the beak(s) to the tubular body of the device, and one or more tendon(s configured to actuate the beak(s) and a tendon actuator tab that may be located at any location along the length of the tube. All or portions of the hypo tube may be rigid or flexible.

According to one embodiment, the constituent components of work element 13, such as a living hinge and beak(s) may be actuated by an internal tube advanced axially in a distal direction. The device may also be made of or comprise other materials, such as plastics, polymers or other suitable materials, which may be suitably configured to form various structures such as the beak(s), tendons, tendon actuation tab(s), internal tube actuator or internal ram element of work assembly or element 13. FIG. 1 illustrates an embodiment of a material delivery device 10, comprising a ratchet actuation element 11, a handle 12 and an extended work element 13. One embodiment of the material delivery device 10, as shown in the figures, may be implemented in a hand-held configuration comprising an ergonomically comfortable and secure handle 12 at its proximal end. Work element or assembly 13, from which material may be delivered to tissue, may be (removably, according to one embodiment) coupled to the handle 12. In this manner, the material delivery device 10 may be easily directed with one hand while the other hand is free to hold a guiding probe such as an ultrasound transducer. According to one embodiment, the device 10 may be configured to fit onto any number of guiding devices such as a stereotactic imaging stage or other guidance modality such as MRI.

As shown, one embodiment of the material delivery device 10 may comprise a work element 13 comprising one or more articulable sharp elements (herein, alternatively and collectively referred to as "beak", "beak assembly" or "beak element" or "beak elements") projecting forward distally for the purpose of forward tissue penetration and material delivery or recovery in a simple point and shoot procedure. According to one embodiment, the handle 12 may comprise and/or be coupled to internal driving components needed to drive the work element 13. As shown, one embodiment may comprise a work element comprising a beak 13 that may comprise one or more sharp cutting tip blades that are configured to penetrate to the target site at or from which materials may be delivered or removed or retrieved. The ability of the device 10 to, according to embodiments, repeatedly deliver multiple materials during a single insertion signifies that, with a single penetration through the skin of a patient, the operator can deliver materials to multiple areas without causing additional trauma that would otherwise be necessary. Indeed, there is significant trauma associated with having to remove a delivery device each time a delivery of a material to a site is made, and associated with repeatedly reintroducing the material delivery device 10 back into the patient to deliver additional materials.

Additionally, when conventional needles are used to multiply deliver materials, during single percutaneous entry (through the skin) there still exists a risk for deeper trauma to internal tissues as well as transfer of foreign material to the target site. Indeed, such transfer is based on the fundamental inherent limitations of using open-ended needles as delivery devices, which are necessarily designed for cutting and, by virtue of their shape, designed to attempt to exclude the ingress of tissue into the lumen during advancement. In contrast, the device according to some embodiments comprises a work element that can be closed (via the beak or beaks) between deliveries. Significantly, this means that, during movement of the present device in deeper tissues, foreign materials are not introduced into the device (as the beak or beaks at the distal portion thereof are in their closed configuration that does not admit tissue into the lumen. Also, embodiments render it unnecessary to "cut and exclude" tissues while moving from site to site as necessarily occurs (by design) when using conventional needles as delivery devices. The present devices and methods ensure minimal trauma and maximize "clean delivery" of only those materials intended to be delivered to the exact target site, and/or restricting the volume of delivered materials precisely to the intended volume (slice, tranche, amount) of material and no more. The handle 12 may also contain and/or be coupled to internal or external mechanical components for the delivery of materials such as, for example, a variety of flushes, medications, tracer materials and/or implantable marker elements through the central lumen of the work element 13.

Material delivery device 10, according to one embodiment, may be configured to have the smallest possible caliber (e.g., diameter) of delivery tube assembly that would be clinically useful. For example, according to one embodiment, the device 10 may be configured to have a range of about 21 gauge to about 8 gauge diameter. The delivery device 10 may be constructed of or comprise flexible materials. The device 10 may have a length sufficient to reach target sites that are distant from the skin surface without the need for a surgical procedure. Such a configuration enables the distal end (the end thereof that is furthest from handle 12) of the material delivery device 10 to reach the targeted site. Embodiments of the present material delivery device 10 may be used by right and/or left-handed persons and in multiple positions and orientations, to enable the present device to be used in areas of limited access and to enable the device 10 to be easily positioned for ideal orientation to perform a material delivery or recovery procedure. The delivery or recovery procedure may be carried out under real time image guidance. All or part of the device 10 may be configured to be disposable and/or may be configured to be reusable in whole or in part. It should be noted that when the device is rotated, the work elements create, by design, a "flashing" reflection when visualized by ultrasound, which is useful, as such "flashing" helps enable precise placement of the device beak tips for precise delivery of the contents of the device, particularly in combination with the significant reduction in resistance to movement of the device through tissues as a result of beaks rotating while closed.

Embodiments of the present material delivery or removal device 10 may be driven by one or more motors and electrically powered by batteries and/or external power sources through a simple electrical coupling placed, for example, in the handle 12 or proximal end of the device 10. The entire device 10 may also be internally or externally manually powered, mechanically powered or be powered by energy stored in a coiled spring or by, for example, compressed air, gas or pressurized fluid. Powering the material delivery device entirely manually may be advantageous in areas in which the electric grid is absent, unavailable, or unreliable.

In FIG. 1, the material delivery device 10 is shown in a pre-penetration configuration with the distal end thereof in a closed configuration. Also shown in the implementation of FIG. 1 is a removable cover 14, a Luer-type connection element 15, a rod element 16 (which may be graduated to indicate materials delivered extending through the Luer connection element), and a pointer adjacent to a graduated actuating wheel 11. The placement of these features is exemplary in nature and embodiments may contain some or all of these features in various locations and configurations.

Figure 2:
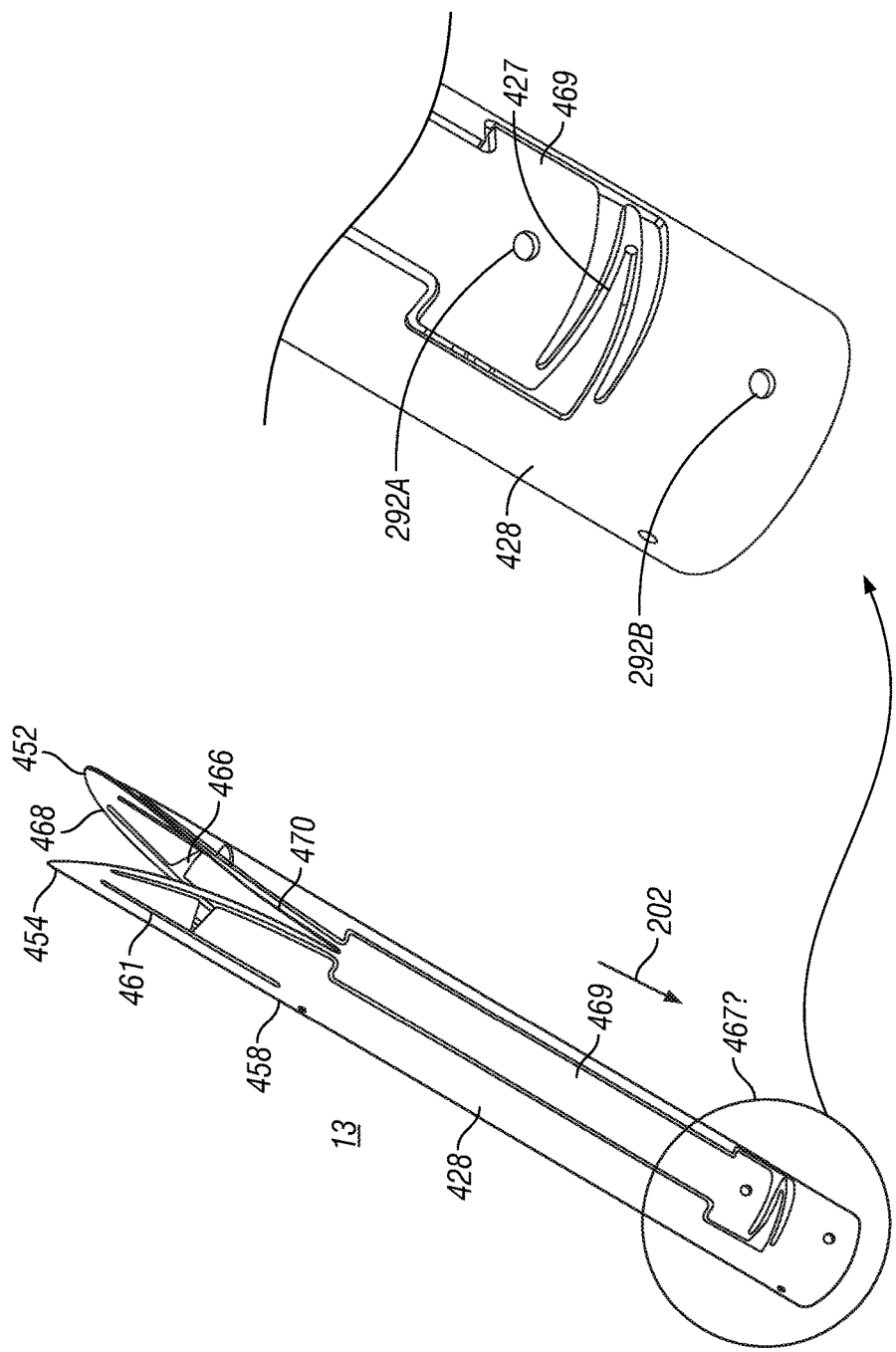
FIGS. 2A and 2B show details of a work element, according to one embodiment.

FIGS. 2A and 2B show an embodiment of a work element 13. Attention is drawn to the proximal end of such a work element 13 at 467. Therein, a body portion 428 of work element 13 may be mechanically coupled to (and/or integral and/or a continuation of) a tendon actuating element 469 at the proximal end of work element 13. Note that tendon actuating element 469, from the embodiment of FIGS. 2A and 2B, is already coupled to the body portion 428 through tendons 468, 470, toward the distal end of a work element 13. That is, the entire work element 13 may be formed of a single homogeneous piece of material—such as from a single hollow tube that is (for example) laser-cut to form the structures shown in FIGS. 2A and 2B. According to one embodiment, each structure formed in the work element is smoothly connected to every other structure in the work element 13, without joints, attachments, overlapping layers, pivot points or couplings of any kind. Stated differently, no structure of work element 13 may be separated from the rest of the work element without cutting into a portion of the original single hollow tube from which the work element was formed.

The embodiment of FIGS. 2A and 2B shows a device 10 having two beaks. It is to be understood, however, that such need not be the case, as work element 13 may comprise multiple beaks or a single beak configured to act against a non-moveable part such as, for example, a fixed beak, trough or scoopula-shaped distal portion of an outer sheath.

According to one embodiment, as shown in FIGS. 2A and 2B, the proximal end of tendon actuating element 469 may be mechanically coupled to the proximal portion of a body portion 428 by an integrated resilient element 427 also, according to one embodiment, formed from the aforementioned single hollow tube. Such mechanical coupling may be configured to maintain the tendon actuating element centered on the cutout in the body portion formed to accommodate tendon actuating element 469 and/or to provide additional biasing force in the distal direction, as well as to aid in manufacturing. One embodiment, as illustrated in FIG. 2B, comprises a resilient member 427 having one end coupled to a tendon actuating element 469 and another end coupled to a proximal portion of the work element 13. Such a resilient member 427 may be configured to bias the beak or beaks 452/454 of work element 13 in the open configuration, such that a sufficiently great proximally-directed force applied to a tendon actuating element 469 and thus to tendon elements 468/470 tends to close a beak or beaks. Conversely, release of such proximally-directed force causes a resilient member 427 to release the energy stored during the compression thereof and return to its less compressed state, thereby exerting a distally-directed force on a tendon actuating member 469, which causes a beak or beaks to return to its or their open configuration, that is, tension in the proximal direction on a tendon actuator tab or tabs causes the beak(s) to close and tension in the distal direction allows the beak(s) to open. According to embodiments, the tendon actuator tab(s) may be normally under tension by any of a variety of structures, including a spring connecting the tendon actuator tab to the main body portion of the tube, an external spring such as element 27 of FIG. 7A acting against a tendon actuator collar. The tendon actuator collar may comprise an elastic outer sheath coated on the exterior of the tube. A control mechanism allows the operator to manually or mechanically open and close the beak(s).

Additionally, wedge-shaped (for example) cutouts 466, and kerfs forming the living hinge 461 may be provided to define one or more articulable beak(s) 452/454 of work element 13, improve the articulation thereof and provide for a greater range of motion. The living hinges may also serve as conduits for medications (anesthetics and epinephrine, for example) and other beneficial liquids, for example, saline flushes, to flow through a central lumen of the device for delivery to the distal end of the device 10, even when beak(s) may be closed during such an intra-operative procedure. According to embodiments, each of a first and second articulable beaks 452, 454 may define a first tendon 468 coupled to one side thereof and a second tendon 470 coupled to the other side thereof. Alternatively, a single tendon may be defined or multiple tendons may be defined. Additionally, according to one embodiment, these tendons may be defined at different relative angles to one another to impose an unequal or asymmetrical force to the sides of the distal end of one or more of the articulable beak tips. As shown, these first and second tendons 468, 470 may be configured to selectively apply a proximally-directed force and a distally-directed force to the distal portion to cause a first and second articulable beaks 452, 454 to assume their closed and open configurations, respectively, or in the case of a single beak configuration, to open or close against a fixed or non-articulable beak. Indeed, pulling on the first and second tendons 468, 470 by a proximally-directed force acting on actuating element 469 tends to close the first and second articulable beaks 452, 454 (i.e., draw the respective distal tips of the beaks closer to the longitudinal axis and closer to one another). Conversely, pushing on the first and second tendons 468, 470 tends to open the first and second articulable beaks 452, 454 (i.e., draw the respective distal tips of the beaks away from the longitudinal axis and away from one another, thereby opening the central lumen of the device 10).

Also shown in FIG. 2B, attachment holes 292A and 292B may be provided on the body portion 428 and on the tendon actuating element 469, respectively. Such attachment holes 292 may, according to embodiments, indicate the location of, for example, spot welds or glue welds, as detailed below.

Turning now to further embodiments and in more detail, the discussion that follows will focus on general features of a whole device 10, which may comprise a distal end consisting of a work element or elements as well as other elements such as suggested by FIG. 1 and as detailed further below, starting from the distal end and continuing to the proximal end of device 10.

Figure 3:
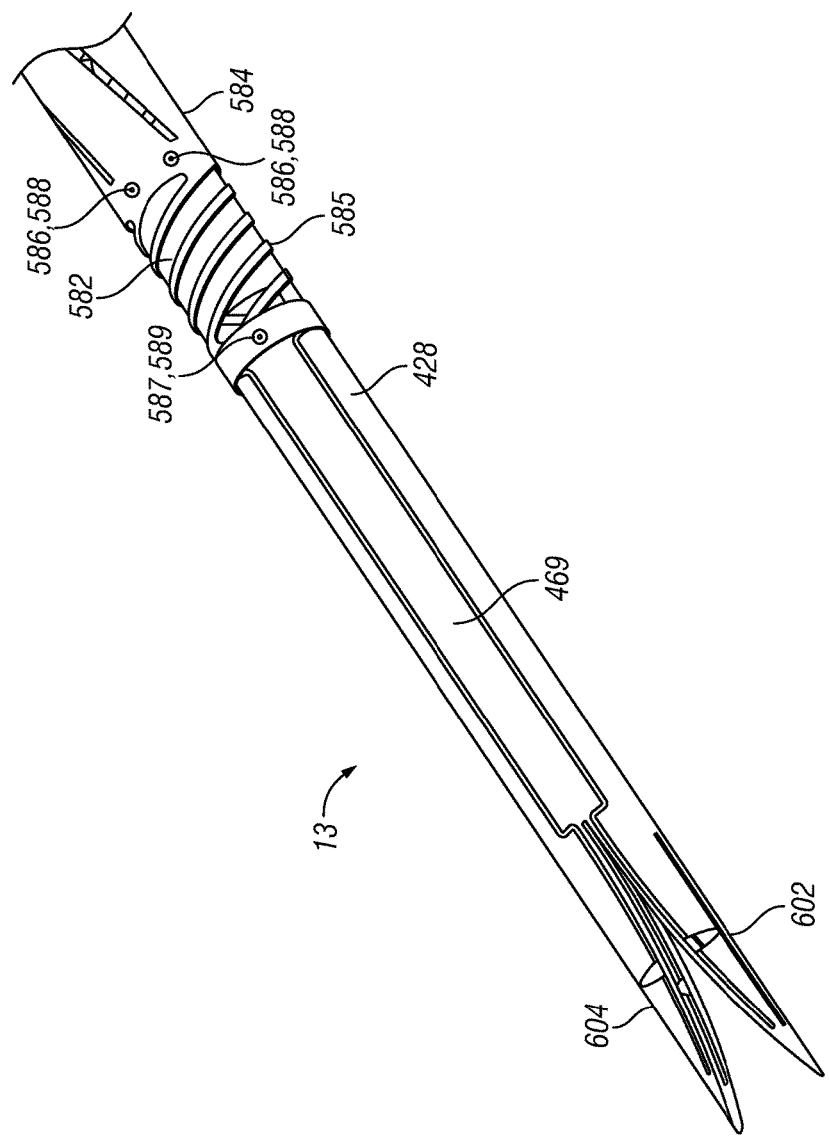
FIG. 3 is a view of a work element comprising first and second beaks, showing an attached outer sheath, according to one embodiment.

FIG. 3 is a view of a two beak work assembly, according to embodiments. FIG. 3 shows components of a work element 13 (comprising, e.g., body portion 428, one of the tendon actuation elements or tabs 469 and first and second articulable beaks 602, 604. The work element 13 may be mechanically coupled to a proximal sheath 584 as an extension of the tubular structure. As suggested at 586, 588 and at 587, 589, a proximal sheath 584 may be spot-welded to the work element 13 in such a manner as to enable differential motion of the body portion 428 of the work element 13 relative to the tendon actuating tabs 469 thereof when the helical element 585 compresses and extends, which differential motion actuates (e.g., opens and closes) first and second articulable beaks 602, 604. Significantly, the attachment of the proximal sheath 584 to both the body portion 428 and to tendon actuating tabs 469 of the work element 13 results in substantially equal torque being imposed on the constituent elements of a work element under rotation, thereby maintaining the structural integrity of the work element 13 as it is used and as first and second articulable beaks 602, 604 cut through variably dense, fibrous and/or vascularized tissues.

Figure 4:
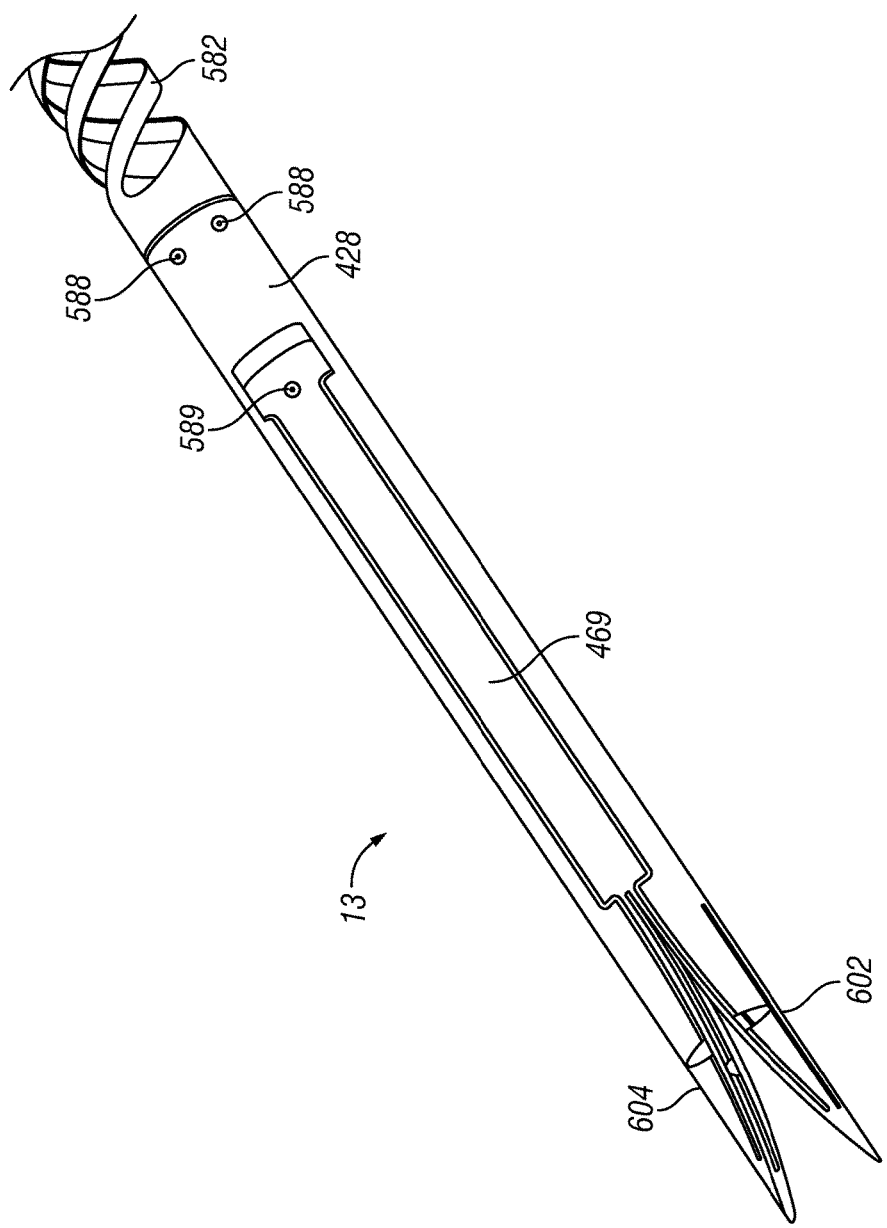
FIG. 4 is a view of a work element comprising first and second beaks with an attached elongated and flexible body element, according to one embodiment.

FIG. 4 is a view of a work element 13 comprising a multiple beak 602, 604 assembly, according to one embodiment. FIG. 4 shows a body portion 428, tendon actuation element 469 and first and second articulable beaks 602, 604 of a work element 13, together with an attached flexible extension element 582, which may simply be an elongation of the body portion 428 and continuous with regard to its structure. An outer sheath, if desired, may be added but is not visible in this view. As shown, a flexible extension element 582 may be co-axially disposed relative to the body portion 428 of work element 13 and may be of the same or substantially the same diameter. As noted above, the work element 13 and the extension element 582 may be formed of, or cut from, a single piece of material such as, for example, a stainless steel hypo tube. According to another embodiment, the flexible extension element 582 may be of a different diameter than the body portion 428.

Figure 5:
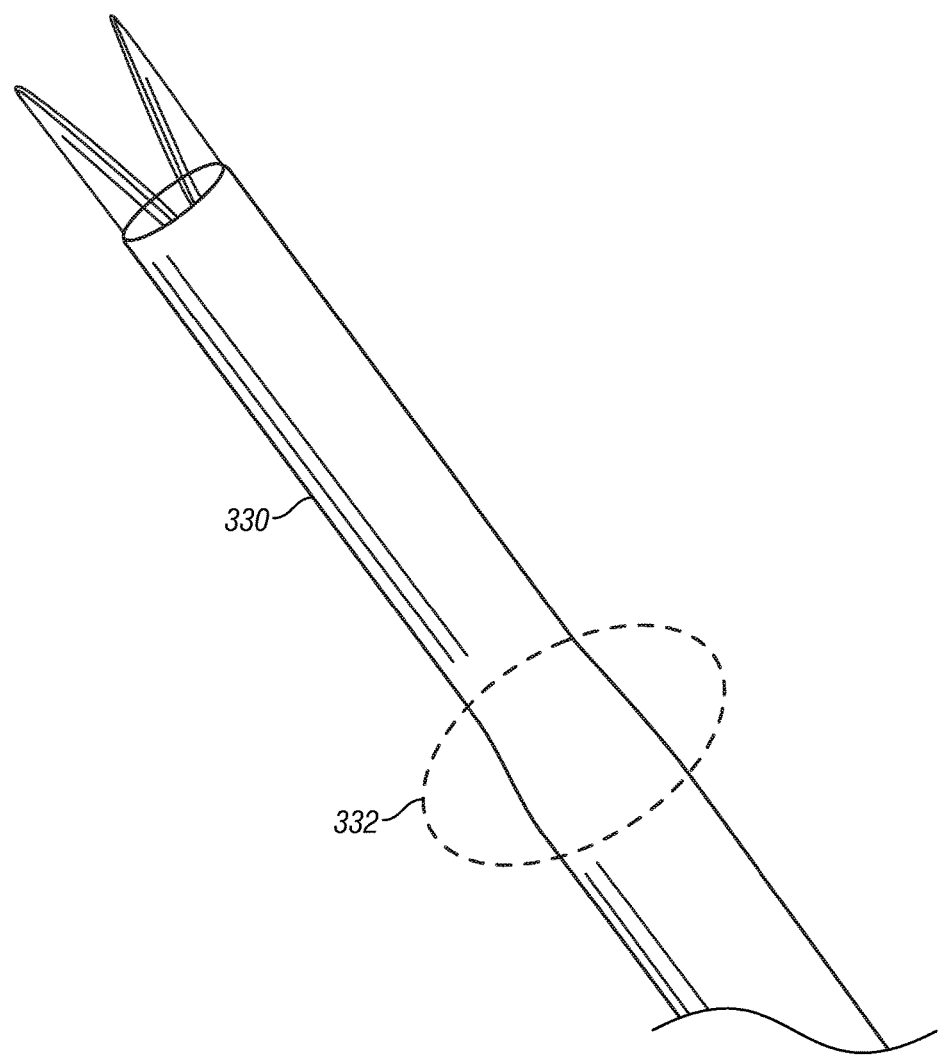
FIG. 5 shows a monolithic beak assembly of a material delivery device with an outer sheath, according to one embodiment.

FIG. 5 shows another embodiment of the work element of the present material delivery device. In FIG. 5, an outer sheath 330 has been fitted over an assembly comprising a monolithic beak assembly. For example, an outer sheath 330 may comprise polyimide or may comprise or be formed of stainless steel or other materials. An outer sheath 330 may be configured to be manually rotating, non-rotating, or at least differentially rotating with respect to an assembly comprising a monolithic beak assembly 13, and may further be configured to be removable. An outer sheath 330 may extend distally to beaks of a monolithic beak assembly 13, may expose a greater proportion of a monolithic beak assembly 13 or may cover a significant portion of beaks, which may be controlled during use, according to embodiments. An outer sheath may have external features such as a spiral to aid in tissue penetration by twisting motions. An outer sheath 330 may also have a first and second dimension with a shoulder 332 between them. According to embodiments, a shoulder 332 could act on a simple collar attached to a tendon actuator tab 469 of FIG. 2B or against an outer tube 584 of FIG. 3 to actuate the beaks of the work element. In another embodiment, the work element 13 previously discussed may be replaced by a single tube, split along its long axis and incorporating travel limiting shapes along the split length of the tube. These travel limiting shapes may be thought of as T-shapes, but other shapes may be selected or envisioned. In such an embodiment, the distal end of one half, arbitrarily, the upper half of the split tube may be attached to a tendon actuation member 469 while the distal end of the opposite (lower) half may be attached to a body portion 428 of a monolithic beak assembly 13. In such a configuration, one half of the split tube acts on tendons of beaks while the opposing half acts on a body portion of a beak assembly or work assembly, thus allowing for axial movement between the upper and lower halves to constitute an actuation mechanism for opening and closing beaks as well as rotation, if desired, since the upper and lower halves of such a split tube necessarily rotate in synchronicity.

Figure 6A:
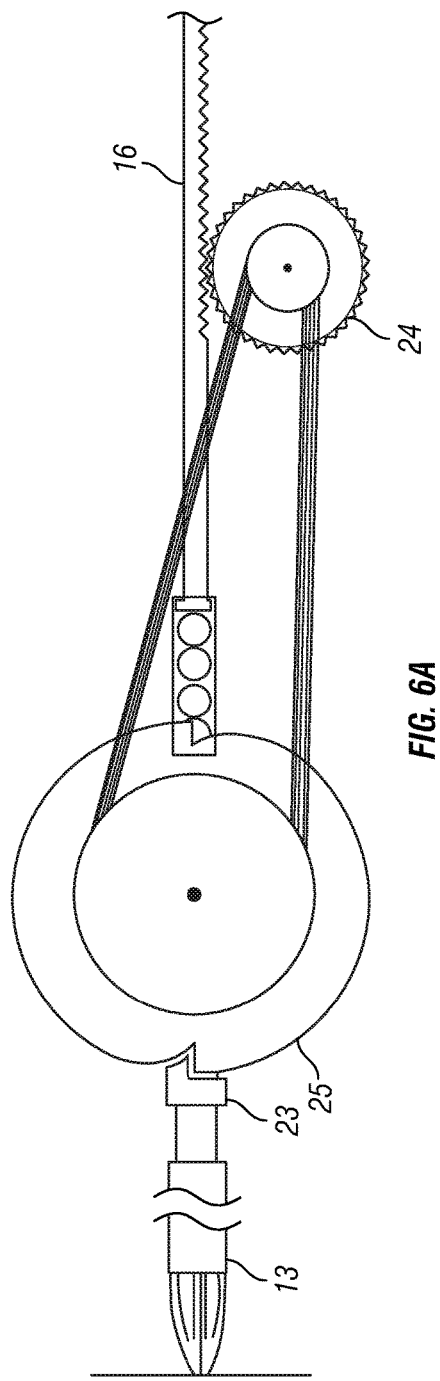
FIGS. 6A and 6B show side perspective details of a monolithic beak assembly and actuation mechanism, according to one embodiment.

FIG. 6A is a side view, not to scale, of an internal driving mechanism for a material delivery device 10, according to one embodiment. FIG. 6A illustrates one phase of operation of a device, according to one embodiment, in which the work element is at rest with beaks in a normally closed position. Having the beaks in a normally closed position eases tissue penetration to a specific target site for material delivery. Maintaining the beaks in a normally closed configuration also secures the material contents within the central lumen of the device 10 until the intended delivery thereof is carried out an operator. Having the beaks in a normally closed position also isolates the contents in the central lumen of the work element from tissue surrounding the work element at any phase, and assures that recovered material will not be inadvertently lost, among other advantages. In the exemplary rendering of FIG. 6A, the material to be delivered to a target tissue site is in the form of round pellets, sequentially pre-loaded into the device with rod element 16 in place to close the proximal end of the work element 13. In this figure, a simple ratchet type mechanism 25 placed at the distal interior end of the handle 12 of device 10 (as an inside mechanism actuated by actuator element 11 of FIG. 1, for instance) may be configured to simultaneously open the beaks of work element 13 and advance the plunger or rod element 16 in pre-selected increments to deliver, for example, single pellets of material at any given moment during a procedure, thus allowing for a series of pellets to be precisely and strategically placed at several locations in a target tissue area by an operator with a single percutaneous insertion, or multiple insertions, of the device 10.

According to one embodiment, the ratchet wheel 25 may have two lands and notches as shown, or may have a greater number of lands (areas of relatively higher elevation) and notches (any localized area of comparatively lower elevation). The device 10 may also comprise an integral pulley configured to drive a rod advancement pinion gear/pulley element 24. For purposes of this illustration, it is assumed that dog element 23 is attached to an extended tendon actuation tab, and that the body portion of the proximal sheath or inner tube is fixed in place in the handle 12, although many other configurations based on the principles and mechanisms described herein may be implemented. As illustrated, if the ratchet wheel 25 is turned counterclockwise, then dog element 23 attached to the tendon actuation tab will ride up onto the land on the circumference of the ratchet wheel, pushing the tendon actuation tab (such as 469 of FIG. 4) distally in relation to the rest of the work element 13 and thus cause the beaks at the distal end of the device to open. Once the dog element 23 reaches the end of the land, upon further rotation of ratchet wheel 25, it will drop into the notch on the circumference of the ratchet wheel 25 and thus allow the beaks to be closed again. The height of an individual land thus corresponds to the axial distance necessary to open or close the beaks of work element 13, and the radial length of each land represents the total time that the beaks will remain open (assuming constant rotational speed of the ratchet wheel 25), thus allowing for precise matching of the simultaneous travel of rod element 16, acted upon in this embodiment by the pulley/pinion gear 24 on the rack of the rod element 16, as it pushes a pellet, in this example, out the end of the opened beaks and just prior to the beaks re-closing. As shown, according to this illustration, a half revolution of the ratchet wheel will fully open and then close the beaks of work element 13. Any number of lands on ratchet wheel 25 may be configured, according to the type of material to be delivered and according to embodiments. For instance, an elongated pellet of material (or two round pellets at a time, for example) may require the beak or beaks of work element 13 to remain open a longer time (longer total individual land radial length) to allow delivery. Different ratchet wheel sizes and corresponding land and notch configurations may be provided (or swapped in as drop-in replacements in the handle 12) to accommodate different materials, sizes and shapes of the item or items to be delivered or retrieved.

As shown in FIG. 1, the actuator 11, connected to the ratchet wheel 25 internally, may be operated by either a left or right handed person, and may be operated by, for example, the operator's thumb pushing the ratchet wheel counterclockwise (pushing forward) from the top of the handle 12 forward for one click, equating to the dog element travelling over one full lands (or pausing in the midpoint of the land, to allow the beaks to remain open), or by the operator's index finger pulling the actuator 11 of FIG. 1, accessible below the handle 12, back one click to deliver precisely one pellet of material at a time. In the embodiment shown, a simple two pulley and belt arrangement allows for simultaneous rotation of the ratchet wheel 23 and the rod element pinion gear 24. A rod element 16 with rack teeth, according to embodiments, may be advanced axially in a distal direction by action of a simple pinion matched to a rack configured on its lower surface. The rod element may be made of plastic, and the various wheels, gears pulleys, dogs and other elements may also be molded of such material, or other material according to embodiments.

Figure 6B:
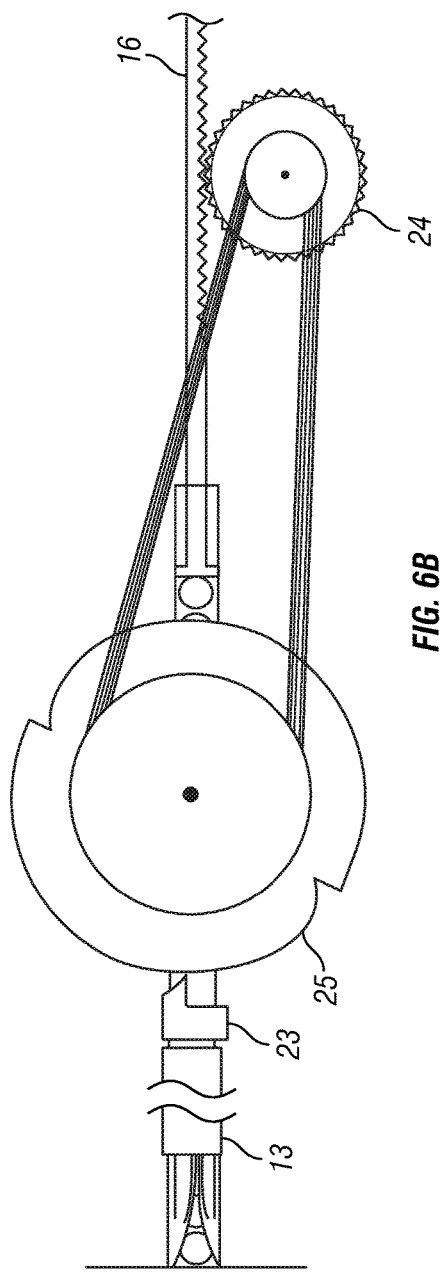

The embodiment illustrated in FIGS. 6A and 6B allows for a virtually unlimited combination of ratchet wheel sizes, number of lands per ratchet wheel, diameter of a pulley attached to the ratchet wheel, diameter of a pulley attached to the rod pinion 24, the diameter of a rod pinion gear 24, the number of teeth on a rod pinion gear, and the teeth on the rod element rack gear to be precisely matched to a specific diameter and morphology of a selected material to be delivered by the device 10. The ability to match beak opening times with material ejection times ensures the positive and precise delivery of the intended payload item or items to be delivered at any given time, and not more or less. For example, the device 10 may be configured to deliver one and only one pellet, for instance, at a time, and the fact that the beaks close after such an incremental delivery ensures that any remaining pellets in the magazine of the central lumen of the device remain captive inside the lumen and not lost or inadvertently delivered to the same location, while also giving an operator a running count of precisely what has and has not been delivered at a given point in time of a procedure (and thus location inside the target tissue area. This feature may be critically important if for example, radio-active pellets are to be precisely delivered around a target cancerous lesion as a therapy option.

Figure 7A:
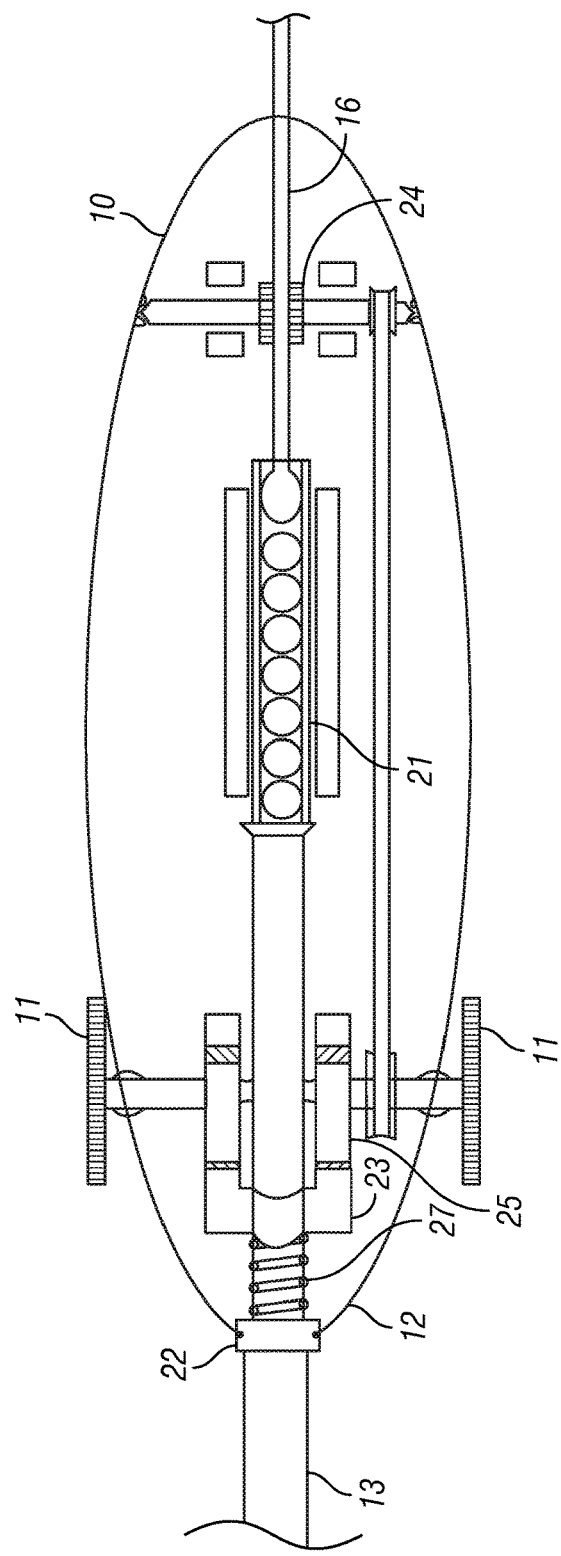
FIG. 7A shows a top perspective view of additional detail of internal elements of a material delivery device, according to one embodiment.
Figure 7B:
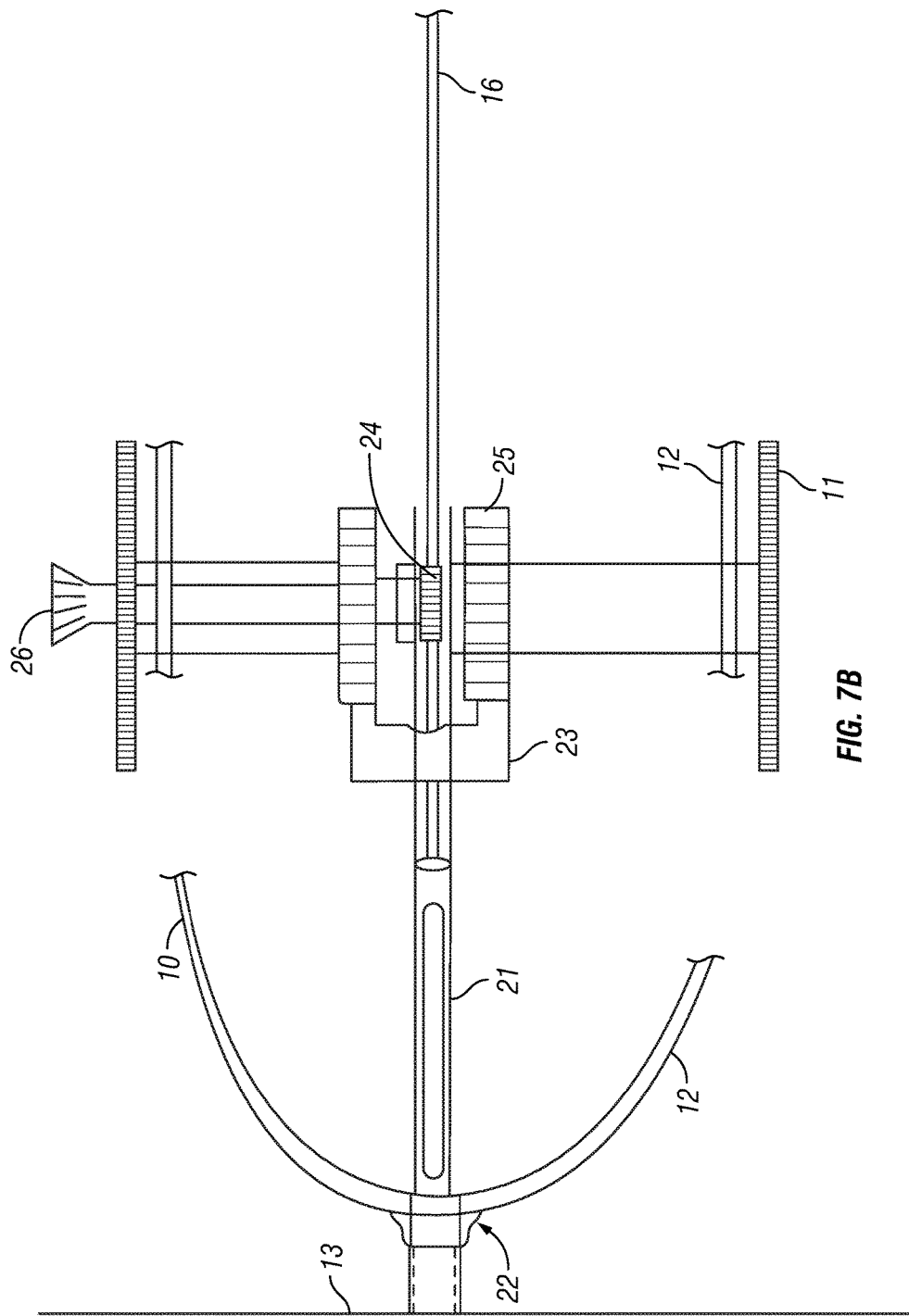
FIG. 7B shows another top perspective view of internal structures of a material delivery device, according to one embodiment.

FIG. 7B illustrates the ratchet wheel mechanism in a later phase of a material delivery procedure in which the beaks of work element 13 are open and in the process of delivering a pellet of material to a target tissue site. Note that the dog element 23 has ridden up onto the land of ratchet wheel 25 to open the beaks, and that the belt between the two pulleys has advanced the rod element 16 simultaneously via the pinion gear 24 acting on the rod element 16 incorporated rack to advance the material to be delivered out of the beak at the distal end of the device 10. If this sequence is continued, at precisely the moment that the pellet has cleared the open beak ends, the dog element 23 will drop into the notch in ratchet wheel 25 and close the beaks to prevent a second pellet from emerging and being delivered before it should be. It should also be noted that since the ratchet wheel 25 in this figure is assumed to be manually operated by actuator element 11 of FIG. 1, the operator may simply decide to pause rotation to keep the beaks open, which may be desirable for liquid material delivery, for example, or to allow passage through the central lumen of the device 10 of imaging devices, such as an OCT scanner or fiber optic or ultrasound imaging systems.

A simple slide lock mechanism mounted on the handle 12 externally may also be provided to allow an operator to engage element 25 to lock the beaks of work element 13 in either a fully open, fully closed or an intermediate position, as desired. It should also be noted that the rod element 16 may be replaced by a tube for liquid or gas delivery, which may be accomplished through the Luer-type connector shown in FIG. 1, and may also allow for vacuum to be applied to the central lumen of the device if material such as liquids or cells at a target site is desired to be removed. Vacuum may also be applied through the Luer-type connection in the case in which the device is used to recuperate previously delivered material in single or sequential fashion, such as radio-active pellets at the end of a scheduled therapy.

FIG. 7A is a top perspective view of a material delivery device 10 with its cover 14 removed from handle 12 to show placement of internal components, according to one embodiment. The internal components in this figure correspond to the elements of the embodiment shown and discussed relative to FIGS. 6A and 6B. This view shows elements such as the dog element 23 riding on the ratchet wheel 25 and actuated by the actuator element 11 external to the handle 12. Also seen are the attached pulleys and belt connecting the ratchet wheel 25 to the rod pinion gear 24, the rod element 16 prepositioned to deliver pellets from a removable and replaceable magazine 21, the spring element 27 which biases the beaks in a normally closed position, according to embodiments, and a collar 22 which, in this embodiment, captures an outer tube of work element 13. The collar may be of a standard external dimension size, such as for example, 8 millimeters, and thus work elements of varying gauges may be quickly substituted in the handle 12. As may be envisioned, the work element, ratchet wheels, rod elements, magazines and other elements may be field-replaceable and swapped out for a drop-in replacement at any time, including intra-procedurally by opening the cover 14, taking out the old components, dropping in the new components and closing the cover 14. Larger gauge work elements configured to accommodate solid materials or items of larger diameter may be provided. Also, for example, in place of the magazine and rod element, a tube for vacuum or liquid delivery (not shown) may be substituted with ease, and the operator may manually open or close the beaks by simple rotation of the actuator 11, which corresponds to that found in FIG. 1.

FIG. 7B illustrates another embodiment of the device 10 from a top-down perspective, wherein the double pulleys of FIG. 7A are not present, and the simultaneous driving of the ratchet wheel 25 and rod element pinion gear 24 are accomplished by rotation of actuator element 11 by the operator from outside of the handle 12. A pinion disengagement element 26 allows disconnection of the pinion gear 24 from the ratchet wheel 25 to allow for changing rod elements—for example, one that is ramrod shaped to one with a pointed tip if desired for tissue penetration external to the work element beaks, or a guide wire to allow for the device to be placed over a guide wire. In this example, according to one embodiment, the magazine 21 is placed forward of the ratchet wheel mechanism, which is opposite to that found in FIG. 7A. In another embodiment, a spring may be disposed over the shaft of the ramrod to create forward pressure against material, such as pellets, loaded into a magazine 21. In this case, the pinion gear 24 and its action may be replaced by that spring and release of the pellets would be controlled solely by the ratchet wheel mechanism 25 itself. In that embodiment, the beak opening and closing time action alone may precisely control the material delivery action.

According to one embodiment, the device may be placed near a target delivery site through the central lumen of another device, such as a biopsy device, that may itself be either forward cutting or side cutting in principle. According to another embodiment, the device may comprise of an inner tube with the monolithic work element and an outer tube may be attached to the tendon actuator tab or acting on a collar attached to the tendon actuator tab. In this implementation, proximally- or distally-directed displacement of one tube in relation to the other will cause the beak(s) to open or close. According to another embodiment, the device may contain a single tube attached to a simple handle mechanism, which may be reusable with replacement device tubes easily fitted to the handle for use. Such a handle may operate simply on the principle of a vertical scissors or clamp action, with one blade attached to the main body portion of a single tube and the other blade attached to the tendon actuation tab for a single tube device, or to an inner tube extending proximally beyond an outer tube. In this implementation, the two blades of the scissors or clamp actuate each of the tubes to cause longitudinal (i.e., proximally or distally-directee0 relative motion to one another, thus causing the beak(s) of the work element to selectively open or close. According to one embodiment, a simple rod element 16 may be used to advance materials to be delivered to and out of the distal end of the device.

The device 10, according to some embodiments, may comprise a single tube device or the device 10 may be a multi-tube device comprising, for example, of an inner and outer tube, which outer tube may have an outer coating. According to some embodiments, such an outer coating may comprise, among other types, a flexible coating that may be sprayed on or into which the tube may be dipped or rolled, a shrink wrap type coating, or other coating that may allow for the delivery of liquids or gases to a target tissue site while preventing body fluids from entering the central lumen of the tube through any laser cuts or kerfs associated with the monolithic beak(s) of the work element at the distal end of the device. Such a coating may also, according to one embodiment, allow for vacuum to be used to drain a target site before, during or after a procedure with the device 10. Once the target site is drained, a tube of the device 10 may be replaced by another that may be preloaded with pellets situated, for example, in the handle 12. The main body of the device may, according to embodiments, be of any suitable length desired, for example, about 4-8 inches in length, and may be flexible to enable such operations as following a vein or artery, or other internal structure or organ. Device features such as beaks, living hinges, tendons, and tendon actuation tabs may be of any length, number or shape, according to embodiments. It is to be understood, however, that the foregoing dimensions and any dimensions referred to herein are exemplary in nature only and are not limiting factors. Those of skill in the art will recognize that other dimensions and/or configurations may be implemented, depending upon the application, and that a tubular material delivery assembly and its subparts could be of any suitable length.

Below is a description of a method of carrying out a material delivery procedure, according to one embodiment. The present in-situ method of material delivery begin with imaging the tissue of the organ or corporeal structure of interest and identifying the target lesion or tissue or structure to which it is desired to deliver a material or materials. For example, the tissue structures of interest may comprise for example, vascular structures or intra-organ structures. The skin may then be cleansed using sterile techniques, and the patient may be draped and anesthetics delivered. The distal tip of the present material delivery or removal device 10 may then be introduced into tissue through a skin nick incision. Further still, a guiding element may be provided so as to be coaxial with, in tandem with or adjacent to the long axis of elements of the material delivery device. The guiding element could alternatively be a completely separable or discrete device, such as a removable outer sheath, with or without a scoopula-shaped extension. Such a scoopula-shaped extension may, according to one embodiment, function as a locating tube, which locating tube may be pre-placed by an operator skilled in imaging and targeting and fixed in place near or within the target tissue or structure. After placement and fixation, an operator may then proceed by advancing the material delivery device 10 over or within a previously precisely placed and anchored guiding element.

Figure 9:
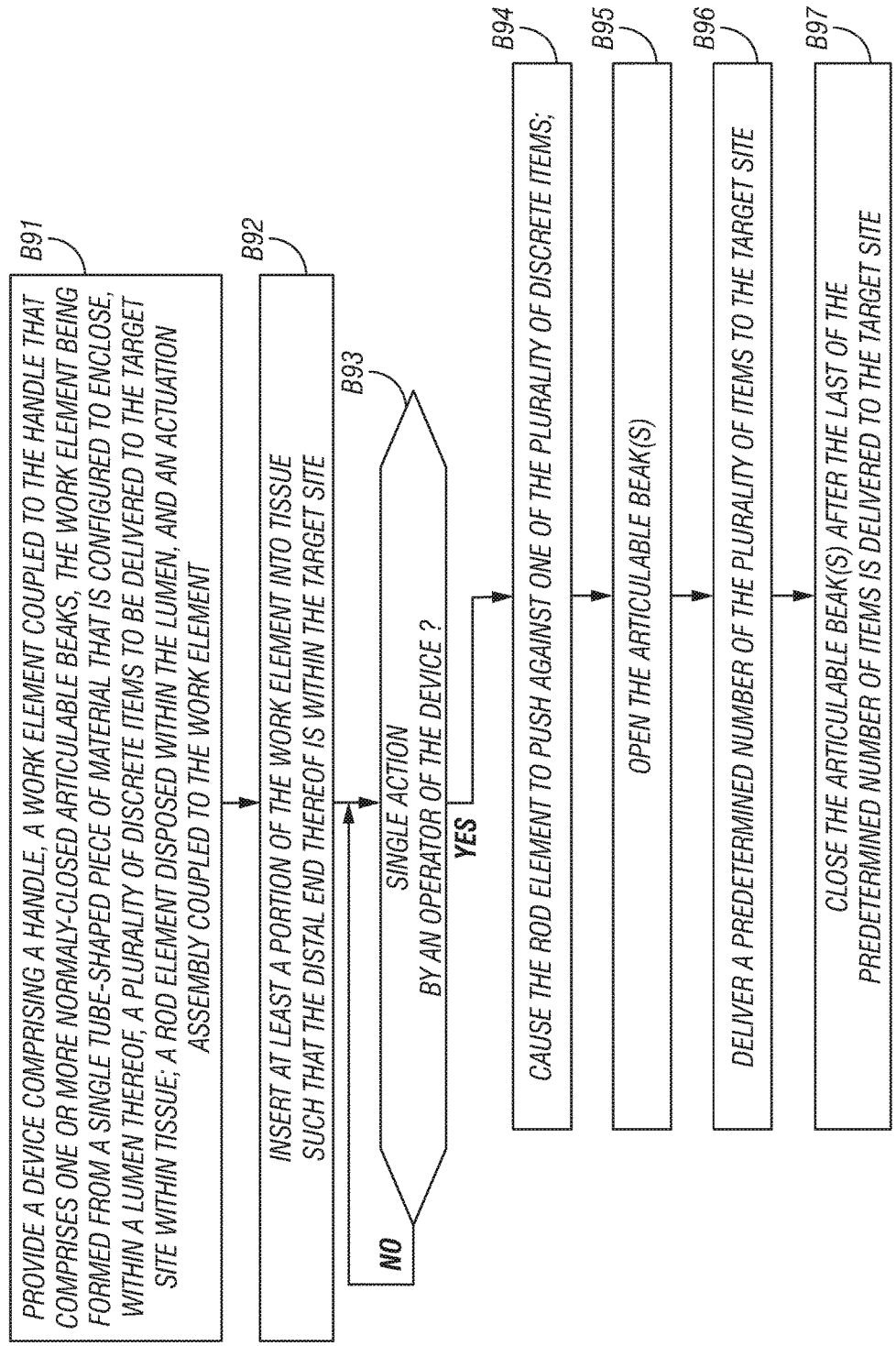
FIG. 9 is a flowchart of a method according to one embodiment.

Additionally, in the case of administering radioactive materials for example, a radiation specialist may be required to deliver the materials. In such a case, once an anchoring/guiding element is placed at or near the target delivery site, the radiation specialist may introduce the material delivery device according to one embodiment, and proceed with delivery of the radiation sources (as shown in FIG. 9, for example), which may comprise decaying implants or removable sources of radiation, for example. If a scoopula-shaped component is used, as shown in FIG. 8A at 802, together with the present device, the scoopula-shaped tip may be placed to precisely define the distal location of a delivered pellet, which then can be ejected (laid down along) away from the open trough segment of the scoopula, in the likewise precise orientation of the scoopula-shaped component, as suggested by pellet 804 in FIG. 8A. This scoopula-shaped component 802 may be made with materials suitable for shielding radiation exposure, such that the scoopula-shaped component 802 may be used to direct radiation in only the desired direction while it is in-situ, shielding unwanted radiation scatter in the direction of sensitive tissues for which radiation exposure might be harmful, and potentially dose limiting for the desired target tissues that are the intended recipients of the therapeutic radiation.

The material delivery device 10 may be advanced percutaneously to the target tissue site. Fluids or anesthetics may be delivered during that process. A further delivery stage may then be initiated to deliver, for example, the contents of a preloaded cartridge of materials or discrete items. For example, such a cartridge may enclose tracer elements like visible dyes, echo-enhancing materials and/or radioactive tracer elements. Alternatively, medications such as epinephrine or anesthetics may be delivered at any stage of the material delivery procedure, either directly through open beaks, through living hinges of closed beaks or via a reverse flow from a flush system built into the device. For typical placement of radioactive pellets, a pattern around a target lesion may be pre-planned, whereupon the radioactive pellets may be dispensed from the distal end of the device one after the other, with precision and in a single insertion, multiple item delivery mode. It should be noted that this same device may readily be used remove tissue or structures or to retrieve previously placed materials, such as radioactive source pellets, in sequential fashion when it has been determined that their function has been fulfilled, in a reverse sequence to that outlined above.

Advantageously, the device may also be used to deliver radiation for a certain "dwell time" after which the radiation source may be withdrawn from the delivery site and recovered back into the device. According to one embodiment, therefore, the device may be made of or comprise suitable radiation-shielding materials, including the distal work element, to prevent leakage and unwanted exposures between dwell time treatments. In this manner, the device functions as a "single insertion, multi-radiation-delivery" device, without actually leaving anything behind other than the radiation dose(s) itself/themselves. As described above, if a scoopula-shaped component is used, such a scoopula-shaped element (802 in FIG. 8A) may be likewise suitably constructed to act as a radiation shield, which may enable higher dose delivery directionally, while directionally protecting structures that may otherwise be harmed by, and potentially limit, the amount of radiation dose desired for a wanted effect on the tissues to be irradiated.

As shown in previous figures and according to some embodiments, a device 10 with a small diameter distal end may be gently placed in proximity to or into a lesion or target tissue site. Clinically and procedurally, the ability of the present material delivery (or recovery) device 10 to advance gently towards a target site provides several advantages. The present method of introducing a small diameter distal sheath, with the closed beak(s) in tissue penetration mode, enables an operator to gently and smoothly approach a target site without requiring excessive manual axially-directed force to be exerted on the present device 10 by the operator or the stereotactic table itself, if used. It is to be noted that when excessive force must be exerted to advance conventional delivery devices through dense tissue, the resultant image provided by guidance modalities may be significantly distorted by the force applied to the device and transferred to the surrounding tissue, which may cause the resultant image to be less distinct or blurred, and which, in turn, makes the material delivery or removal procedure less accurate and much more difficult technically. Additionally, the work element may comprise materials and structures configured to create a "flashing" reflection during imaging, which, when coupled with the ease of powered penetration, enhances imaging and thus further augments precise placement. It is an important goal of all material delivery or removal procedures to firmly establish that precisely the right quantity of the material delivered has been placed into the highly specific imaged area with extreme precision, notwithstanding the constraints imposed by the small dimensions of the target tissue or structure.

According to some embodiments, the device 10 may comprise flush and liquid/solid materials delivery mechanisms. Such mechanisms may comprise a distal tube socket/flush port such as the Luer connection element 15, which may deliver flush fluids to the distal end of the device. Flush fluids and other materials may thus be delivered to the tissue or structure site through the central lumen of the device, with the beak(s) of the work element 13 in its or their closed configuration (as described for liquids relative to FIG. 2A through living hinge slots) or open configuration. As previously described, various slots and mechanisms such as the open beak(s) may be used in conjunction with flush fluids to gather and transport cells and liquids from the tissue site for later cytological analysis.

It is to be understood that the above descriptions are but exemplary methodologies and that one or more of the steps described above may be omitted, while other steps may be added thereto, depending on the target site within the body, or other operator methodologies. The order of some of the steps may be changed, according to the procedure.

According to embodiments, if the beak(s) are held in the normally closed position, delivery of materials to a target site may be accomplished using a plunger or ramrod that may simply press, for example, a pellet preloaded in the work element 13 of the device 10 out the end of the device through the beaks(s) by overcoming the elastic resistance of the tendon actuator tab in its normally closed position, or the resistance of a living hinge if tendons and actuator are not present. Additionally, in the case of a rod-type radiation source for example, the rod (shown at 802 in FIG. 8A, if the pellet 802 is imagined to be longer and rod-like) may open and enable the beaks to close as it is slid distally for exposure, and then back proximally to shut down delivery (exposure). In this case, beaks remain open during radiation dwell, then close down again as the radiation source-rod is withdrawn back into shielded position within the device. This mechanism also enables the device to be stored securely, preloaded with its radiation source, in the radiation department (this control is required by law) and after transport to and from the treatment suite by licensed radiation safety personnel, safely discarded in the radiation safety department as a unit according to appropriate radiation management procedures. In addition, the in-storage (on the "shelf") decay may be tracked by opening the beaks for example, within the radiation department unless the half-life is already firmly established, in which case the device may be used when within the effective time range only.

FIG. 8B shows another embodiment of a material delivery device 10. According to one embodiment, the work element 13 may comprise an extruded tubular shape comprising a material such as a hard plastic, for example having a tapered distal end. Beaks and living hinges may be formed by scoring the tapered end, with such scores either extending from the outer surface to the inner surface, or simply superficially scored on the external surface. If scored on the external surface, the beaks may be opened by action of an internal element, such as a rod element 16 or internal tube (not shown) acting on, for example, a pellet 18, and the scored surface, previously sealed, will be broken or tear open. Alternatively, fully cut beak slots may be sealed with a wax or other sealing substance or coating, which may be easily ruptured when axial force against the inner surface of the beaks causes them to extend to an open position. Thermally-degradable wax may also be used, according to one embodiment. Such embodiments may be advantageous in delivering liquids or semi-liquids to a target tissue site, with the work element pre-loaded with such materials, while remaining sealed until needed. An internal tube may be provided that may actuate the beaks by a distally-directed axial force, with either sealed or unsealed beaks. Such an embodiment enables a complete sealing of the work element's central lumen (acting as a liner) for delivery of liquids, for example. In such an embodiment, regardless of the method of construction of the work element, there would be no occasion for leaks en-route to a target tissue site or in removing a material, such as a liquid, from a target tissue site.

FIG. 9 is a flowchart of a method according to one embodiment. As shown, Block B91 calls for providing a device comprising a handle and a work element coupled to the handle. The handle may comprise one or more normally closed (e.g., biased to remain in the closed configuration until a sufficient force acts upon it/them) articulable beaks. The work element, as described herein, may be formed from a single tube-shaped piece of material. According to one embodiment, every structure of the work element is connected to every other structure in the work element in an uninterrupted manner by remaining material (e.g., not removed material by laser cutting) of the original tube-shaped piece of material. The work element may be configured to enclose, within a lumen thereof, a plurality of discrete items (medications, radioactive or other biologically-active or beneficial items) to be delivered to a target site within tissue. A rod element may be disposed at least partially within the lumen and an actuation assembly may be coupled to the work element. As shown in B92, at least a portion of the work element may then be inserted into tissue such that a distal end thereof is disposed within the target site. The device, as suggested at B93, is further configured to, responsive to a single action carried out on the device (e.g., when the actuator element 11 turns responsive to operator action), carry out Blocks B94 to B97. Blocks B94-B97 are not carried out until that first single action by the operator, as suggested by "NO" branch of B93. Responsive to the single first action by an operator of the device ("YES" branch of B93), the rod element is caused to push against one of the plurality of discrete items (e.g., the proximal-most one in contact with the rod) as shown at B94, the beaks(s) open as shown at B95, a predetermined (e.g., precisely one, precisely two or precisely three, for example) number of the plurality of items are delivered to the target site and the beaks(s) close after the last of the predetermined number of items is delivered to the target site. Blocks B94-B97 are carried out without further operator interaction, after the aforementioned single action by the operator, according to one embodiment.

The present material delivery device may be formed of or comprise one or more biocompatible materials such as, for example, stainless steel or other biocompatible alloys, and may be made of, comprise or be coated with polymers and/or biopolymer materials or other materials as needed to optimize function(s). For example, the elements (such as the constituent elements of a beak assembly 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components. Additionally, radiation shielding materials may be incorporated into certain components, such that these may act as shields both during storage and transport of the entire device and for certain procedures that may benefit from for example, directional shielding in-situ (in the tissues). The various internal components may be made of any suitable, commercially available materials such as nylons, polymers such as moldable plastics, and others. The handle of the present material delivery or removal device may likewise be made of or comprise inexpensive, injection-molded plastic or other suitable rigid, easily hand held strong and lightweight material. The handle may be configured in such a way as to make it easily adaptable to one of any number of existing guiding platforms, such as stereotactic table stages. The materials used in the present material delivery or removal device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present material delivery or removal device in this manner may then be ejected into an additional external, yet portable, liquid storage vessel connected to the tubing of the present material delivery or removal device, for safe keeping or for laboratory cellular analysis.

The beak assembly of embodiments of the material delivery or removal device may be used, without alteration of its shape, attachment or any other modification, to penetrate tissue on approach to a target site for material delivery. The beak assembly of the work element may then be used to open and temporarily or permanently deliver the material desired to the target tissue site. The beak assembly may also be used to help capture and transport any collected materials, including previously placed materials, or fluids or cells for later analysis. Having such multiple functions integrated in a single device saves valuable cross-sectional area, which in turn creates a device that has a minimal outer diameter while providing the maximum inner diameter for materials to be delivered.

Integral and detachable components may be provided and configured to aspirate fluids for cellular analysis as well as deliver materials or other devices at various selectable stages of the procedure. The present material delivery or removal device may be selectable for automatic and/or semi-automatic function, may be used with or without image guidance, and may be compatible with a variety of guidance imaging equipment such as ultrasound, magnetic resonance imaging, OCT and X-ray imaging. The present material delivery or removal device may be configured to be disposable and/or recyclable, highly portable, and delivered for use in sterile packaging, typical of medical devices having contact with internal body structures. The present material delivery or removal device may be configured to be minimally invasive. As embodied herein, the present material delivery or removal device comprises several features that may be therapeutic in nature, to be utilized at various stages along the diagnosis/treatment pathway.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
   a handle;
   a work element coupled to the handle, the work element defining a proximal end closest to the handle and a distal end furthest from the handle, the work element comprising at least one articulable beak that is normally closed, the work element being formed from a single tube-shaped piece of material and configured to enclose, within a lumen thereof, a plurality of discrete items to be delivered to a target site within tissue;
   a rod element partially engaged within the lumen from the proximal end thereof and configured to contact and push against one of the plurality of discrete items to be delivered; and
   an actuation assembly coupled to the work element and configured to selectively open the at least one articulable beak and cause the rod element to push and deliver a predetermined number of the discrete items out from the distal end of the work element to the target site before enabling the at least one articulable beak to close, and a dog element coupled to the work element and a manually rotatable ratchet wheel disposed against the dog element and comprising a plurality of land portions and a plurality of notch portions, such that the at least one articulable beak remains closed when the dog element is engaged within one of the notch portions and is pushed open when the ratchet wheel is rotated such that the dog element rides on one of the land portions.

2. The device of claim 1, wherein the actuation assembly is configured to be manually turned, pushed or pulled in pre-selected increments to enable an operator of the device to cause the delivery of only the predetermined number of discrete items.

3. The device of claim 1, wherein the actuation assembly further comprises a first manually rotatable assembly configured to cause the at least one articulable beak to open and deliver only the predetermined number of discrete items to the target site before closing.

4. The device of claim 1, wherein rod comprises a rack and wherein the actuation assembly comprises a corresponding pinion coupled to the rack, the pinion being configured to rotate and cause the rod element to push against the plurality of discrete elements.

5. The device of claim 1, wherein the actuation assembly is partially enclosed by the handle and comprises a manually-operable portion at least partially external to the handle.

6. The device of claim 1, wherein the rod element is configured to be removable to enable one of an occlusion-crossing rod and a guidewire to be inserted into the lumen of the work element.

7. The device of claim 1, wherein the at least one articulable beak is configured to flex via a portion of the single tube-shaped piece of material configured as a living hinge.

8. The device of claim 1, further comprising a plurality of cuts defined in the work element to define the at least one articulable beak.

9. The device of claim 1, further comprising a plurality of cuts defined in the work element to define the at least one articulable beak, at least one tendon and at least one tendon actuating tab coupled to the at least one articulable beak and to the at least one tendon.

10. The device of claim 1, further comprising one of an outer tube or covering disposed over at least a portion of the work element.

11. The device of claim 1, wherein the work element is formed by selective removal of material from the single tube-shaped piece of material.

12. A device, comprising:
a handle;
a work element coupled to the handle, the work element defining a proximal end closest to the handle and a distal end furthest from the handle, the work element comprising at least one articulable beak that is normally closed, the work element being formed from a single tube-shaped piece of material comprising a plurality of cuts to define the at least one articulable beak, at least one tendon and at least one tendon actuating tab coupled to the at least one articulable beak and to the at least one tendon, the at least one articulable beak being configured to enclose, within a lumen thereof, a plurality of discrete items to be delivered to a target site within tissue;

a rod element partially engaged within the lumen from the proximal end thereof and configured to contact and push against one of the plurality of discrete items to be delivered; and an actuation assembly coupled to the work element and configured to selectively open the at least one articulable beak and cause the rod element to push and deliver a predetermined number of the discrete items out from the distal end of the work element to the target site before enabling the at least one articulable beak to close.

13. The device of claim 12, wherein the actuation assembly is configured to be manually turned, pushed or pulled in pre-selected increments to enable an operator of the device to cause the delivery of only the predetermined number of discrete items.

14. The device of claim 12, wherein the actuation assembly further comprises a first manually rotatable assembly configured to cause the at least one articulable beak to open and deliver only the predetermined number of discrete items to the target site before closing.

15. The device of claim 12, further comprising a dog element coupled to the work element and a manually rotatable ratchet wheel disposed against the dog element and comprising a plurality of land portions and a plurality of notch portions, such that the at least one beak remains closed when the dog element is engaged within one of the notch portions and is pushed open when the ratchet wheel is rotated such that the dog element rides on one of the land portions.

16. The device of claim 12, wherein rod comprises a rack and wherein the actuation assembly comprises a corresponding pinion coupled to the rack, the pinion being configured to rotate and cause the rod element to push against the plurality of discrete elements.

17. The device of claim 12, wherein the actuation assembly is partially enclosed by the handle and comprises a manually-operable portion at least partially external to the handle.

18. The device of claim 12, wherein the rod element is configured to be removable to enable one of an occlusion-crossing rod and a guidewire to be inserted into the lumen of the work element.

19. The device of claim 12, wherein the at least one articulable beak is configured to flex via a portion of the single tube-shaped piece of material configured as a living hinge.

20. The device of claim 12, wherein the work element is formed by selective removal of material from the single tube-shaped piece of material.

* * * * *